United States Patent

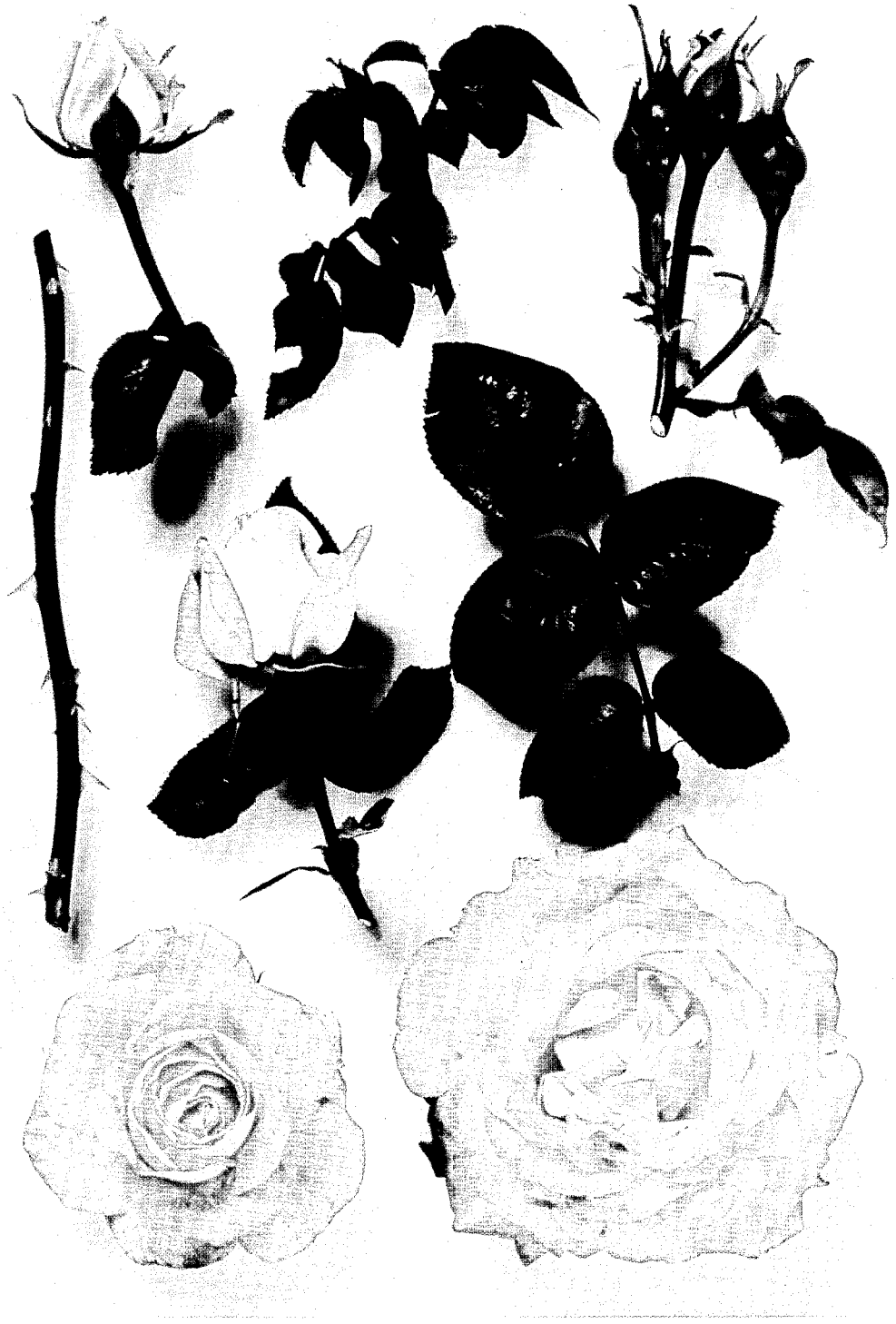

Plant Pat. 3,956

Patented Oct. 12, 1976

3,956

ROSE PLANT

William A. Warriner, Tustin, Calif., assignor to Jackson & Perkins Co., Medford, Oreg.

Filed Sept. 18, 1975, Ser. No. 614,504

Int. Cl.[2] A01H 5/00

U.S. Cl. Plt.—11 1 Claim

The present invention relates to a new and distinct cultivar of rose plant of the hybrid tea class which was originated by me by crossing the cultivar Tropicana, U.S. Plant Pat. No. 1,696 with pollen from the cultivar, Peace, U.S. Plant Pat. No. 591.

The primary objective of this breeding was to produce a new rose cultivar embodying the good characteristics of both parents bearing flowers of a novel multicolor nature. This objective was substantially achieved along with other desirable improvements as evidenced by the following unique combination of characteristics which are outstanding in the new cultivar and which distinguish it from its parents as well as from all other cultivars of which I am aware:

1. A vigorous, well branched habit of growth, similar in appearance to the cultivar Peace.
2. Foliage of the form and color of the cultivar Peace, but with a less glossy upper surface.
3. Flowers are bicolored, being a mottled Carmine on most of the upper face of the petals, and Chinese Yellow on the lower face.
4. The bud and flower form are similar to those of the cultivar Peace.
5. Little or no fragrance.

Asexual reproduction of this new cultivar by budding as performed at Wasco, Calif., shows that the foregoing characteristics and distinctions come true to form and are established and transmitted through succeeding propagations.

The acompanying illustration shows typical specimens of the vegetative growth and flowers of this new cultivar in different stages of development, depicted in color as nearly true as it is reasonably possible to make the same in a color illustration of this character.

The following is a detailed description of my new rose cultivar with color terminology in accordance with Wilson's Horticultural Color Chart, except where ordinary dictionary significance of color is indicated.

Parentage: Seedling.
- *Seed parent.*—Tropicana, U.S. Plant Pat. 1969.
- *Pollen parent.*—Peace, U.S. Plant Pat. 591.

Classification:
- *Botanical.*—Rosa hybrid.
- *Commercial.*—Hybrid tea.

FLOWER

Observations made from specimens grown at Irvine, Calif. August 1975.

Blooming habit: Continuous.

Bud:
- *Size.*—1" to 1¼" when petals start to unfurl.
- *Form.*—Short, pointed, globular.
- *Color.*—When sepals first divide—near Chinese Yellow (606/1); a streak between sepals usually reddened to a color ranging from near Orient Red (819/3) to Garnet Brown (00918/3). When half blown; upper side of petals mottled pattern of Carmine (21) overlaying Chinese Yelolw (606/1).

Base of petal has a large area of Primrose Yellow (601). Lower side of petals from near Chinese Yellow (606/3) to Primrose Yellow (601) at petal base.
- *Sepals.*—Color: Outer surface Scheeles Green (860/3). Inner surface covered with short tomentum. Three appendaged sepals lightly appendaged. Two unappendaged sepals hairy edged.
- *Receptacle.*—Color: Scheeles Green (860/3). Shape: funnel. Size: Small. Surface: Smooth.
- *Peduncle.*—Length: Short. Surface: Glandular near basal end. Color: Light green. Strength: Stiff, erect.
- *Opening.*—Petals curl spiral fashion, but remain only slightly curled when fully open.

Bloom:
- *Size.*—Large Average open size 3" to 4".
- *Borne.*—Singly or several together.
- *Stems.*—Long to medium.
- *Form.*—When first open, high centered. Permanence: Outer petal edges slightly curled.
- *Petalage.*—Number of petals under normal conditions approximately 40.
- *Color.*—Center of flower: Upper side of petals near Carmine (21/1) in a heavily mottled pattern over a color near Chinese Yellow (606/3). Reverse side of petals entirely near Chinese Yellow (606/3). Base of petals Carmine becomes gradually less mottled, that is less Carmine, at middle of petal. Basal one/third of petal is a color near Primrose Yellow (601). General tonality from a distance Carmine (21/1) with Chinese Yellow (606/3) very evident where lower side of petal is exposed.
- *Variegations.*—As noted above.
- *Discoloration.*—General tonality at end of third day. The carmine color lightens to near Carmine (21/3), the Chinese Yellow (606/3) becomes near white.
- *Fragrance.*—None.

Petals:
- *Texture.*—Thick.
- *Shape.*—Round.
- *Form.*—Edges slightly quilled.
- *Arrangement.*—Imbricated. Petaloids in center, few.
- *Persistence.*—Drop off cleanly.
- *Lastingness.*—On the plant—long. As cut flower—long.

Reproductive parts:
- *Stamens, anthers.*—Medium. Color—yellow. Arrangement—regular around styles.
- *Filaments (threads).*—Color—yellow.
- *Pollen.*—Lemon yellow.
- *Styles.*—Color—near white.
- *Stigmas.*—Color—pale yellow.

PLANT

Form: Bush.

Growth: Vigorous, upright, branching, similar in growth habit to pollen parent.

Foliage: Number of leaflets on normal mid-stem leaves, 5.
- *Size.*—Large.
- *Quantity.*—Normal.
- *Color.*—New Foliage: Garnet Brown (00918/3). Old Foliage: Slightly darker and bluer than Spinach Green (0960).
- *Shape.*—Oval pointed.
- *Texture.*—Upper side—glossy.
- *Edge.*—Serrated.
- *Serration.*—Single.

*Petiole (rachis).*—Color—Reddish. Underside—prickles.

*Stipules.*—Medium, broad, bearded.

*Disease resistance.*—Normally resistant to mildew under normal growing conditions at Irvine, Calif.

Wood:

*New wood.*—Color—Garnet Brown (00918/3). Bark—Smooth.

*Old wood.*—Color—green, sometimes darkened with Garnet Brown. Bark Smooth.

Prickles:

*Quantity.*—On main stalks from base—usually few. On laterals from stalk—few.

*Form.*—Narrow base, long, hooked downward.

*Color when young.*—Brown to yellow.

*Position.*—Irregular.

Small prickles:

*Quantity.*—On main stalks—few. On laterals—few.

*Color.*—Brown.

I claim:

1. A new and distinct cultivar of rose plant of the hybrid tea class, substantially as herein shown and described, characterized particularly as to novelty by the unique combination of its vigorous, well branched growth, its bicolored flowers of mottled Carmine on upper face and Chinese Yellow on lower face, with a bud and flower form similar to those of the cultivar Peace, and little or no fragrance.

No references cited.

ROBERT E. BAGWILL, Primary Examiner